United States Patent [19]

Ding et al.

[11] Patent Number: 5,081,281

[45] Date of Patent: Jan. 14, 1992

[54] PROCESS FOR THE PREPARATION OF 3,3',4,4'-BIPHENYLTETRACARBOXYLIC ACID AND ITS DERIVATIVES

[75] Inventors: Mengxian Ding; Zugiang Wang; Zhenghua Yang; Jing Zhang, all of Changchun, China

[73] Assignee: Changchun Institute of Applied Chemistry, Changchun, China

[21] Appl. No.: 418,059

[22] Filed: Oct. 6, 1989

[30] Foreign Application Priority Data

Oct. 11, 1988 [CN] China ................. 8817107.2

[51] Int. Cl.$^5$ ........................... C07C 67/343
[52] U.S. Cl. ..................... 560/96; 560/76; 562/488
[58] Field of Search ............. 560/76, 96; 562/488

[56] References Cited

U.S. PATENT DOCUMENTS

| | | | |
|---|---|---|---|
| 4,263,466 | 4/1981 | Colon et al. | 585/421 |
| 4,294,976 | 10/1981 | Itatani et al. | 560/76 |
| 4,338,456 | 7/1982 | Itatani et al. | 560/96 |
| 4,581,469 | 4/1986 | Itatani et al. | 560/96 |

FOREIGN PATENT DOCUMENTS

| | | |
|---|---|---|
| 48-52749 | 7/1973 | Japan . |
| 55-020705 | 2/1980 | Japan . |
| 55-141417 | 5/1980 | Japan . |
| 60-051151 | 3/1985 | Japan . |
| 61-22044 | 1/1986 | Japan . |

OTHER PUBLICATIONS

Colon et al., *Journal of Organic Chemistry*, vol. 51, #14, (1986), pp. 2627-2637.
Takagi et al., *Bull. Chem. Soc. Japan*, 57 pp. 1887, 1890, (1984).

Primary Examiner—Jose G. Dees
Assistant Examiner—Vera C. Clarke
Attorney, Agent, or Firm—James F. Tao; Arthur S. Cookfair

[57] ABSTRACT

Biphenyl tetracarboxlic acid esters and derivatives thereof are prepared by the coupling reaction of 4-halogen substituted o-benzenedicarboxylic acid ester, carried out in an aprotic polar solvent in the presence of a pre-prepared triphenylphosphine-nickel chloride or trialkylphosphine-nickel chloride catalyst, zinc powder as the reducing agent, and an alkali metal halide promoting agent. The ester may be hydrolyzed in basic solution to afford the corresponding acid. The acid may be heated or boiled with acetic anhydride to afford the biphenyl dianhydride.

28 Claims, No Drawings

PROCESS FOR THE PREPARATION OF 3,3',4,4'-BIPHENYLTETRACARBOXYLIC ACID AND ITS DERIVATIVES

This invention relates to a method for the synthesis of 3,3',4,4'-biphenyltetracarboxylic acid and its derivatives. The tetra carboxylic acid, as well as the dianhydride thereof, are useful chemical intermediates for the further preparation of various compounds, including, for example, the salts, esters, acyl halides, amides, imides, and the like. The compound 3,3',4,4'-biphenyltetracarboxylic acid (hereinafter referred to as biphenyltetra acid) and the corresponding dianhydride are particularly useful in the preparation of high performance polyimides, for example, by polycondensation with a suitable diamine, such as ethylenediamine or phenylenediamine. In addition, the biphenyltetra acids and dianhydrides prepared in accordance with this invention are useful as curing agents for epoxy resins.

The preparation of biphenyltetra acid using a palladium catalyst has been reported in the literature (Japanese Patents: 7352749, 80141417, 8551151, 8020705). Furthermore, the coupling reaction of halogenated aromatics has been disclosed using Ni(O) catalyst and reducing agent (Zn, Mn, Mg). For example in 1981, I. Colon et al of Union Carbide reported a coupling reaction of mono chlorides of aromatics and heteroaromatics using triphenyl-phosphine, nickel chloride, zinc powder as reducing agent and inorganic salt as promoting agent [U.S. Pat. No. 4,263,466 (1981)]. However, they did not apply the process directly to the preparation of biphenyltetra acid. In a subsequent paper (Colon et al, Journal of Organic Chemistry, Vol. 51, No. 14 (1986) p. 2627-2637) disclosed coupling reactions of chloroaromatics using both triarylphosphine and trialkyl phosphine as ligands in a reaction mixture containing nickel chloride, sodium halide promoter, and zinc. The authors found that triaryl phosphines were the best ligands. Trialkyl phosphines gave much slower reactions and lower yields, even when the ligands were used in large excess. In 1984, K. Takagi et al also reported that using pre-prepared trialkylphosphine-nickel halide catalyst, potassium iodide as promoting agent, bromoaromatics and iodoaromatics underwent coupling reaction with good yields [Bull. Chem. Soc., Japan, 57. 1887 (1984)]. However, they reported a very low yield of the coupled product when using chlorobenzene as the starting material. In 1986, Hitachi Company reported a coupling reaction using halogenated o-benzenedicarboxylic acid ester as the starting material, tetrakis (triphenylphosphine) nickel (0) complex, tetrakis (triphenylphosphine) palladium (0) as the catalyst, and zinc as the reducing agent. Subsequently, the coupled product was hydrolyzed to afford biphenyltetra acid (Japan Patent 6122034).

It has now been found that biphenyltetracarboxylic acid esters and derivatives thereof, may be prepared by the coupling reaction of 4-halogen substituted o-benzenedicarboxylic acid ester, carried out in an aprotic polar solvent in the presence of a pre-prepared nickel complex of triphenylphosphine and/or trialkylphosphine as the catalyst, zinc powder as the reducing agent, and alkali metal halide as the promoting agent to yield biphenyltetracarboxylic acid ester. The ester may then be hydrolyzed in basic solution to afford the biphenyltetra acid. The acid, upon heating or boiling with acetic anhydride, will afford biphenyldianhydride.

It is an advantage of this invention that the pre-prepared $(Ar_3P)_2NiX_2$ or $(Alk_3P)_2NiX_2$ catalyst (where X is chlorine or bromine; Ar is aryl; and Alk is alkyl) is more stable in air than the $(Ph_3P)_4Ni(O)$. In the pre-prepared catalysts employed in the present invention, only 2 equivalents of triaryl phosphine or trialkyl phosphine per mole of nickel halide are required. Therefor, it is a specific advantage of this invention is that it does not require the addition of excess amount of the expensive triphenylphosphine or trialkylphosphine ligand during the reaction.

The 4-halogen substituted o-benzenedicarboxylic acid ester starting material for the process of the present invention may be conveniently prepared by reaction of the corresponding 4-halogen substituted phthalic anhydride with a lower alcohol under acid-catalyzed conditions. The ester is then coupled in accordance with the invention, using as a pre-prepared catalyst, $(Ar_3P)_2NiX_2$ or $(Al_3P)_2NiX_2$ in an aprotic solvent. The yield of the biphenyltetra acid ester can reach 90% or higher. The tetra ester may be hydrolyzed in a basic solution and acidified to afford the corresponding tetra acid. The acid, upon heating or boiling with acetic anhydride, will form biphenyldianhydride.

The starting materials for the process of this invention are esters of 4-halophthalic acid. They may be conveniently prepared by the reaction of a 4-halophthalic anhydride, preferably 4-chloro- or 4-bromophthalic anhydride with suitable alcohol, preferably an alkanol of 1-6 carbon atoms, in the presence of a mineral acid such as hydrochloric acid, sulfuric acid, toluenesulfonic acid, or the like, typically at temperatures of about 70°-160° Celsius.

The coupling reaction of the invention may be illustrated by the following equation:

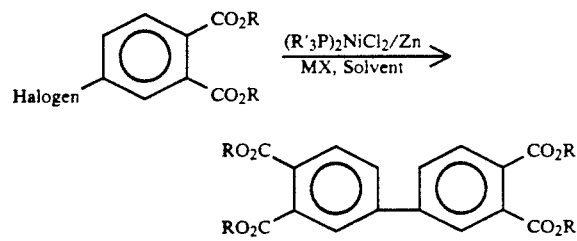

where R is preferably alkyl of 1-6 carbon atoms, most preferably 1-4 carbon atoms; R' is alkyl, cyclic alkyl, aryl alkyl or alkoxy substituted aryl, wherein the alkyl or alkoxy groups are 1-12 carbon atoms and aryl is 6-10 carbon atoms. Preferably R' is alkyl of 1-4 carbon atoms; and MX is an inorganic salt, preferably an alkali metal halide, most preferably sodium bromide. The inorganic salt is typically employed in an amount of about 100 to 600 mol percent based on the amount of 4-halophthalic acid ester starting reactant. The solvent employed is preferably a polar, aprotic solvent, such as dimethyl formamide (DMF), dimethyl acetamide (DMAC), N-methyl pyrrolidone (NMP), dimethyl sulfoxide (DMSO), hexamethyl phosphoramide (HMPA) or the like. Preferably, the solvent is employed in an amount of about 2 to 10 ml/g of reactant. The zinc is employed in powder form, preferably in amounts of about 100 to 400 mol percent based on the amount of 4-halophthalic acid ester starting reactant. The temperature at which the coupling reaction is carried out may vary considerably but is typically in the range of about 20°-100° C. and preferably about 40°-100° and most preferably 40°-60° Celsius. The reaction time may run, for example, as long as 48 hours or more, but will typically be in the range of about 1 to 8 hours.

The amount of $(R'_3P)_2NiCl_2$ catalyst is preferably about 1 to 10 mol percent, based on the amount of 4-halophthalic acid ester starting reactant. The catalyst may be purchased commercially or may be prepared in a known manner, for example, by the reaction of triphenylphosphine or trialkylphosphine with nickel chloride in a suitable solvent such as ethanol. Methods of preparation of catalysts, suitable for use in the process of this invention are set forth in Jensen et al, Acta Chem. Scand. 17 (1963) No. 4, and in Doughty et al, Journal of the American Chemical Society 101:10 (1979), the disclosures of which are incorporated herein by reference. The preferred catalysts are the complexes of trialkyl phosphine and nickel chloride, most preferably wherein the alkyl group is 1-4 carbon atoms. The trialkyl phosphine/nickel chloride catalysts have been found particularly advantageous due to ease of removal of the catalyst residue from the reaction product. This is particularly important for the preparation of biphenyltetra acid esters and derivatives of high purity to be employed in the further preparation of high performance polyimides. In addition, it has been found that the use of trialkyl phosphine complexes results in less exotherm during reaction, thus making the reaction temperature more easily controlled.

The following examples are provided to further illustrate the invention and the manner in which it may be practiced. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

A mixture of 4-chlorophthalic anhydride (80 g, 95% purity) and 320 ml methanol was heated to reflux in a round bottom flask. Anhydrous HCl gas was added into the solution slowly, with stirring. After 6 hours, the addition of HCl was stopped and most of the methanol was removed by distillation. To the residue, was added 500 ml of $H_2O$, followed by extraction with $HCHl_3$. The organic layer was washed three times with saturated $Na_2CO_3$ and twice with saturated NaCl, then dried over anhydrous $MgSO_4$. $CHCl_3$ was removed on a rotary evaporator and the residue was distilled at reduced pressure to afford 95.07 g (95% yield, B.P. 110°-120° C./10 mm).

EXAMPLE 2

To a three-necked flask, was added 5.25 g of triphenylphosphine $Ph_3P$ (20 mmol) and 25 ml of glacial acetic acid. The mixture was heated under nitrogen to dissolve all the $Ph_3P$. The solution was cooled to room temperature and 2.37 g of $NiCl_2.6H_2O$ (10 mmol) in 2 ml of $H_2O$ was added. Glacial acetic acid (50 ml) was added. Large amounts of olive green crystals precipitated out from the solution. The solution was continuously stirred overnight. The crystals turned to dark blue color. The mixture was filtered. The precipitate was washed twice with glacial acetic acid and dried under vacuum to afford 5.5 g (84% yield) of $(Ph_3P)_2.NiCl_2$.

EXAMPLE 3

Into a nitrogen-flushed reaction flask, under $N_2$ atmosphere, was added 4.50 g (20 mmol) of dimethyl 4-chloro-benzenedicarboxylate (CBDM) 5.2 g (20 mmol) of anhydrous NaBr, 2.68 g (40 mmol) zinc powder and 0.52 g (0.8 mmol) $(Ph_3P)_2.NiCl_2$. The mixture was maintained under a nitrogen atmosphere while 30 ml of DMAC, dried over molecular sieves was added. The mixture was heated with stirring to 80.C in one hour. The color of the solution turned from bluish-green to brown in 0 5 hours. After 4 hours, the solution was cooled, filtered and the solvent was removed on a rotary evaporator. Chloroform was added and the solution filtered again. The filtrate was washed three times with saturated aqueous NaCl. $CHCl_3$ was removed. 50 ml of 20% NaOH solution was added to the residue and and the mixtures was heated to reflux for 4 hours. The mixture was filtered and the filtrate was acidified with concentrated hydrochloric acid. A white precipitate formed, was filtered, washed with $H_2O$ several times, and dried in an oven at 100° C. to afford 3.2 g of biphenyltetracarboxylic acid (97% yield). The tetra acid was heated slowly to 210°-220° C. to dehydrate and afford biphenyldianhydride, m.p. 299°-302° C.

EXAMPLE 4

Into a reaction flask was added, under $N_2$, 2.28 g (10 mmol) of CBDM, 2.6 g (20 mmol) of NaBr, 0.67 g (10 mmol) of zinc powder, 0.26 g (0.4 mmol) of $NiCl_2(PPh_3)_2$ and 20 ml of dried DMAC. The mixture was heated, with stirring, to 80° C. for 18 hours, then cooled and filtered. DMAC was removed at reduced pressure and $CHCl_3$ was added and the mixture filtered again. The filtrate was washed three times with a saturated NaCl solution, and dried over anhydrous $MgSO_4$. GC analysis of the sample indicated 93.9% biphenyltetra ester, 1.8% CBDM and 4.3% benzene diester (reduced product).

EXAMPLE 5

Into a reaction flask was added, under $N_2$, 4.56 g (20 mmol) of CBDM, 6.6 g (40 mmol) of anhydrous KI, 1.34 g (20 mmol) of zinc powder and 0.52 g (0.8 mmol) of $(Ph_3P)_2NiCl_2$. NMP (40 ml), distilled over $CaH_2$, was added to the mixture. The solution was heated to 80° C. for 7 hours. The brown mixture was combined with a dilute HCl solution and extracted with $CHCl_3$. The organic layer was washed three times with a saturated NaCl solution, dried over anhydrous $MgSO_4$, and filtered. $CHCl_3$ was removed on a rotevap. The residue was hydrolyzed with 50 ml of 20% NaOH, then acidified to afford 2.2 g of the biphenyltetra acid (66.6% yield).

EXAMPLE 6

The procedure of Example 5 was repeated except that in place of the $(Ph_3P)_2NiCl_2$ there was substituted 0.29 g (0.8 mmol) of triethylphosphine-nickel chloride $(Et_3P)_2$acid (63.6% yield).

EXAMPLE 7

Into a reaction flask was added, under $N_2$, 22.8 g (100 mmol) of CBDM, 26 g (200 mmol) of anhydrous NaBr, 13.4 g (200 mmol) of zinc powder and 2.6 g (4.0 mmol) of $(Ph_3P)_2NiCl_2$. To the mixture, was added 150 ml of dried DMAC. The solution was heated with stirring to 60° C. over a one hour period and maintained at that temperature for 4 hours. The mixture was then filtered and the filter cake was washed with DMAC three times. DMAC was removed from the filtrate. To the residue was added 100 ml of anhydrous EtOH and small amount of activated carbon. The mixture was heated to boiling, filtered while hot, and the filtrate cooled. The resultant white crystal was recrystallized twice in EtOH and dried to afford 16 g of biphenyl tetraester (83%) m.p. 97°-99° C.

EXAMPLE 8

Following the procedure of Example 3, 2.73 g (10 mmol) of 4-bromobenzenedicarboxylic acid methyl ester, 0.26 g (0.4 mmol) of $(Ph_3P)_2NiCl_2$, w.6 g (20 mmol) of NaBr and 1.34 g (20 mmol) of zinc powder in 20 ml of DMAC afforded 1.38 g biphenyltetra acid (83.6%), m.p. 297°-301° C.

EXAMPLE 9

To a flask were added 4.56 g (20 mmol) of dimethyl 4-chlorophthalate, 5.2 g (20 mmol) of anhydrous sodium bromide, 2.68 g (40 mmol) of zinc dust and 0.27 g (0.8 mmol) of Bis(tributylphosphine)nickel chloride. After purging with nitrogen, 30 ml of dry DMAC was added via a syringe. The mixture was heated, with stirring, to 70° C. over a one hour period, and reaction conditions were maintained for an additional 5 hours. After cooling the reaction mixture was filtered. The filtrate was distilled under reduced pressure to remove DMAC. Chloroform was added and the mixture was filtered again. The filtrate was washed three times with aqueous sodium chloride solution. The yield of 70.6% of tetraester was determined by gas chromatography.

EXAMPLE 10

The following procedure was carried out for purposes of comparison: A mixture of 0.11 g (0.17 mmol) of anhydrous nickel chloride, 0.49 g (0.6 mmol) of tributylphosphine, 5.2 g (20 mmol) of anhydrous sodium bromide and 2.86 g (40 mmol) of zinc dust was added to a flask. After purging with nitrogen, 10 ml of dry DMAC was added via syringe. The mixture was stirred and maintained at room temperature for 0.5 hour. A solution of 4.56 g (20 mmol) of dimethyl 4-chlorophthalate in 20 ml of dry DMAC was slowly added. The reaction was carried out at 70° C. for 10 hours. The reaction mixture was treated as mentioned in Example 3 to give 0.7 g (21.2%) of biphenyltetracarboxylic acid.

EXAMPLE 11

A mixture of 12.6 g of dibutyl-4-chlorophthalate, 8.2 g of anhydrous sodium bromide, 4.0 g of zinc dust, and 1.0 g of tributylphosphine-nickel chloride [$(Bu_3P)_2Ni(II)Cl_2$] in 30.0 g of DMF was heated and maintained at 50° C., with stirring, for a period of 9 hours. Analysis of the reaction product by gas chromatography indicated 86.69% (g.c. area %) of biphenyltetrabutyl ester.

EXAMPLE 12

The procedure of Example 11 was repeated except that the reaction temperature was maintained at 60° C. and the reaction product was analyzed after a 6 hour reaction period and found to contain 87% (g.c. area %) of biphenyltetrabutyl ester.

EXAMPLE 13

The procedure of Examples 11 and 12 was repeated except that the reaction was carried out at 70° C. over a period of 6.25 hours. The reaction product contained, in g.c. area %, 86.52% biphenyltetrabutyl ester.

EXAMPLE 14

A mixture of 4.5 g of dimethyl-4-chlorophthalate, 0.6 g of sodium chloride, 2.7 g of zinc dust, and 0.3 g of pre-prepared triethylphosphine-nickel chloride catalyst [$(Et_3P)_2NiCl_2$] in 28.3 g of dimethylformamide, wad heated, with stirring, in a nitrogen atmosphere, and maintained at 80° C. for 5 hours to yield a reaction mixture containing, in g.c. area %, 77.4% of biphenyltetramethyl ester. The temperature was raised to 100° C. and maintained for an additional hour, to yield a reaction product containing, in g.c. area %, 86.7% biphenyltetramethyl ester.

EXAMPLE 15

The following procedure was carried out for purposes of comparison: A mixture of 45.0 g of dimethyl-4-chlorophthalate, 7.3 g of sodium chloride, 15.4 g of zinc ddst, 0.5 g of nickel chloride, and 3.5 g of triethyl phosphine, in 70.8 g of dimethyl formamide was heated, with stirring, in a nitrogen atmosphere, and maintained at 77°-80° C. for 5.5 hours, to yield a reaction product containing, in g.c. area %, 13% of biphenyltetramethyl ester.

What is claimed:

1. A process for the preparation of biphenyltetracarboxylic acid ester of the formula

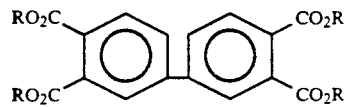

where R is alkyl of 1-6 carbon atoms, which comprises the coupling reaction of 4-halophthalic acid ester of the formula

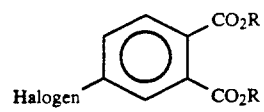

wherein R is as defined above, carried out at a temperature of about 20° to 100° Celsius in a polar aprotic solvent in the presence of:
  (A) a pre-prepared $(R'_3P)_2NiCl_2$ catalyst, wherein R' is alkyl, or cyclic alkyl of 1-12 carbon atoms, aryl of 6-10 carbon atoms or alkyl or alkoxy-substituted aryl;
  (B) zinc powder; and
  (C) an alkali metal halide.

2. A process according to claim 1 wherein the pre-prepared catalyst is a complex of nickel chloride and triphenylphosphine of the formula $(R'_3P)_2NiCl_2$ wherein R' is phenyl.

3. A process according to claim 2 wherein the 4-halophthalic acid ester is a 4-chlorophthalic acid ester.

4. A process according to claim 3 wherein the 4-halophthalic acid ester is a 4-chlorophthalic acid ester of the formula

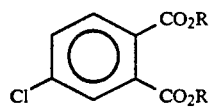

wherein R is alkyl of 1–4 carbon atoms.

5. A process according to claim 4 wherein the 4-chlorophthalic acid ester is dimethyl 4-chlorophthalate.

6. A process according to claim 4 wherein the alkali metal halide is sodium bromide.

7. A process according to claim 4 wherein the alkali metal halide is sodium chloride.

8. A process according to claim 1 wherein the pre-prepared catalyst is a complex of nickel chloride and trialkylphosphine of the formula $(R'_3P)_2NiCl_2$ wherein R' is alkyl of 1–12 carbon atoms.

9. A process according to claim 8 wherein the 4-halophthalic acid ester is a 4-chlorophthalic acid ester.

10. A process according to claim 9 wherein the 4-halophthalic acid ester is of the formula

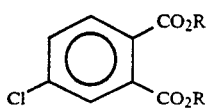

wherein R is alkyl of 1–4 carbon atoms.

11. A process according to claim 8 wherein the 4-halophthalic acid ester is dimethyl 4-chlorophthalate.

12. A process according to claim 9 wherein the 4-halophthalic acid ester is dibutyl 4-chlorophthalate.

13. A process according to claim 9 wherein the 4-halophthalic acid ester is diethyl 4-chlorophthalte.

14. A process according to claim 10 wherein the alkali metal halide is sodium bromide.

15. A process according to claim 1 carried out at a temperature of about 40° to 60° Celsius.

16. A process according to claim 1 with an additional step of hydrolyzing the biphenyltetracarboxylic acid ester produced, in a basic solution, to form the corresponding biphenyltetracarboxylic acid.

17. A process according to claim 16 wherein the biphenyltetracarboxylic acid produced is dehydrated to form the corresponding biphenyl dianhydride.

18. A process for the preparation of biphenyltetracarboxylic acid esters of the formula

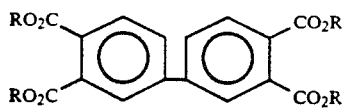

where R is alkyl of 1–4 carbon atoms, which comprises the coupling reaction of 4-chlorophthalic acid ester of the formula

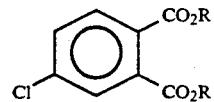

wherein R is as defined above, carried out in a polar aprotic solvent in the presence of:
(A) a pre-prepared $(R'_3P)_2NiCl_2$ catalyst, wherein R' is phenyl;
(B) zinc powder; and
(C) an alkali metal bromide.

19. A process according to claim 18 carried out at a temperature of about 40° to 100° Celsius.

20. A process according to claim 19 wherein the catalyst is present in the amount of about 1–10 mol percent, zinc is present in an amount of about 100 to 400 mol percent and the alkali metal bromide is present in an amount of about 100 to 600 mol percent, based on the amount of 4-chlorophthalic acid ester starting reactant.

21. A process for the preparation of biphenyltetracarboxylic acid ester of the formula

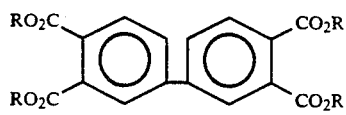

where R is alkyl of 1–4 carbon atoms, which comprises the coupling reaction of 4-halophthalic acid ester of the formula

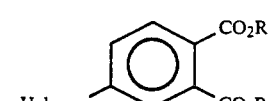

wherein R is as defined above, carried out in a polar aprotic solvent in the presence of:
(A) a pre-prepared $(R'_3P)_2NiCl_2$ catalyst, wherein R' is alkyl of 1–4 carbon atoms;
(B) zinc powder; and
(C) an alkali metal bromide.

22. A process according to claim 21 carried out at a temperature of about 40° to 100° Celsius.

23. A process according to claim 21 wherein the solvent is dimethylformamide.

24. A process according to claim 22 wherein the catalyst is present in an amount of about 1–10 mol percent, zinc is present in an amount of about 100 to 400 mol percent and the alkali metal bromide is present in an amount of about 100 to 600 mol percent, based on the amount of 4-halophthalic acid ester starting reactant.

25. A process according to claim 24 wherein the alkali metal bromide is sodium bromide.

26. A process according to claim 24 wherein the 4-halophthalic acid ester is dimethyl 4-chlorophthalate.

27. A process according to claim 24 wherein the 4-halophthalic acid ester is diethyl 4-chlorophthalate.

28. A process according to claim 24 wherein the 4-halophthalic acid ester is dibutyl 4-chlorophthalate.

* * * * *